United States Patent [19]

Fitzke

[11] 4,294,352

[45] Oct. 13, 1981

[54] CATASTROPHIC-EXPOSURE EMERGENCY KIT

[76] Inventor: Rudolf Fitzke, Mariannenplatz 2, 1000 Berlin 36, Fed. Rep. of Germany

[21] Appl. No.: 154,090

[22] Filed: May 28, 1980

[30] Foreign Application Priority Data

May 31, 1979 [DE] Fed. Rep. of Germany ....... 2922507

[51] Int. Cl.³ .................... B65D 85/18; B65D 85/56; B65D 81/00
[52] U.S. Cl. .................... 206/223; 206/803; 150/52 R; 2/1
[58] Field of Search ...................... 206/223, 803, 216; 150/52 R; 2/1

[56] References Cited

U.S. PATENT DOCUMENTS

| | | | |
|---|---|---|---|
| 2,676,319 | 4/1954 | Davidson et al. | 2/1 |
| 2,678,444 | 5/1954 | Howerton | 2/1 |
| 2,794,186 | 6/1957 | Butters | 2/1 |
| 3,132,344 | 5/1964 | Langdon | 150/52 R |
| 3,389,784 | 6/1968 | Hendricks et al. | 206/803 |

*Primary Examiner*—William T. Dixson, Jr.
*Attorney, Agent, or Firm*—Karl F. Ross

[57] ABSTRACT

An emergency kit contains a metallized foil punch adapted to form a cap for the user and containing a metallized foil sheet in the form of a poncho, the foils having gold metallized outer surfaces to facilitate detection and silver metallized inner surfaces for maximum retention of body heat. The pouch also contains a supply of vitamins.

2 Claims, 2 Drawing Figures

CATASTROPHIC-EXPOSURE EMERGENCY KIT

FIELD OF THE INVENTION

This invention relates to a protective kit to be used in emergencies involving catastrophic exposure and suitable for trips, drives and hikes.

BACKGROUND OF THE INVENTION

Catastrophies caused by adverse weather conditions occur with relative frequency and have often deadly consequences for people who must face them unprepared. Protective all-weather clothing and victuals in quantities sufficient to secure the survival of people cut off from rest of the world for several days are usually very voluminous and characterized by a weight such that only experienced travelers would take them along and only then if they know that they must reckon with adverse weather conditions.

OBJECT OF THE INVENTION

The object of the invention is to provide a catastrophic-exposure emergency kit so small and light that anybody without exception, who undertakes a trip into uninhabited areas or goes on a hike into the open countryside, can conveniently take it along and thus provide for himself the absolute certitude of survival for a few days at least even in situations which would otherwise prove catastrophic.

SUMMARY OF THE INVENTION

The instant invention accomplishes this by making use of a flat, folded foil metallized on both sides, large enough to fully enwrap the human body and a packaged vitamin compound, both of which are contained in a pouch.

The catastrophic-exposure emergency kit is extremely light; its weight need not exceed 200 grs. and it can provide to the user who enwraps himself with the foil metallized on both sides secure insulation against heat loss even in extremely low temperatures. The vitamin compounds included with the kit in the form of pills assure, as has been proved by experience, a survival for several weeks even in the event of parsimonious dosage and the absence of other food supplies.

Furthermore, the foil of the instant invention offers a high degree of security to the exposure victim as will be demonstrated hereinafter.

Advantageously, the foil is metallized in such a manner that it will have a silver color on one side and a gold color on the other. The exposure victim, following instructions received with the kit, enwraps his body with the foil turning the silver-colored surface inwardly towards himself and allowing the gold-colored surface to face the exterior. This arrangement provides a very important advantage, namely the total reflection of the radiation emanating from the user's body by the silver-colored metallized surface. Furthermore, the thermal conductivity of the foil, preferably made of a plastic material, is so small that no significant heat loss can occur. The gold-colored exterior surface helps rescuers to locate with ease the person wrapped in the foil by means of radar scanners, as the latter are known to pick up signals reflected from auric metallic surfaces with more precision than from others.

In further development of the instant invention, the handling of the foil supplied with the catastrophic-exposure emergency kit can be greatly facilitated by providing a hole in the center of the rectangular foil for passing the head of the user. The subject may then wrap himself into the foil so arranged simply in the manner of a poncho, requiring only minimal dexterity to cover himself with the lateral segments of the foil. The head is protected by covering it with the pouch in which the catastrophic-exposure emergency kit was held in readiness. This pouch also, is made of foil having a silver-colored metallic finish on the inside and a gold-colored metallic finish on the outside.

The catastrophic-exposure emergency kit according to the instant invention also provides good protection to victims of heat exposure, who in great heat, as would be found in a desert for instance, would have to wait for succor unprotected, or else see themselves exposed to the risk of perishing.

BRIEF DESCRIPTION OF THE DRAWING

The invention is further clarified with reference to the accompanying drawing in which.

SPECIFIC DESCRIPTION

Figure 1:
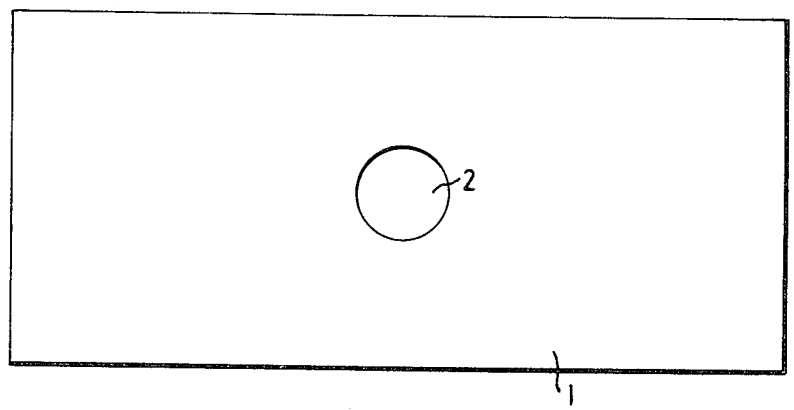
FIG. 1 is a top view of the foil according to the invention.

The foil 1 of FIG. 1 cut in a rectangular shape, is provided with a central opening 2 for the passing through of the head, so that the foil 1 rests in the manner of a poncho on the front and back of the user's body after having been pulled over the head.

Figure 2:
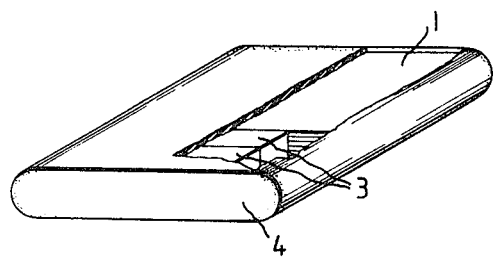
FIG. 2 is a perspective representation of the catastrophic-exposure emergency kit according to the instant invention.

The foil 1 is folded and placed in the pouch 4 dimensioned to form a cap for the user's head, together with a discretionary vitamin compound 3, shown only diagrammatically in FIG. 2 of the drawing, for the purpose of being preventively carried along. The size and weight of a catastrophic-emergency exposure kit of this type are so small that it can be taken along by the traveler without any noticeable increase in the size of his baggage. It will fit into the glove compartment of subcompact automobiles and can be carried in handbags. As hiking apparel is generally tailored for convenience, the catastrophic-exposure emergency kit of the instant invention can simply be stuck into the pocket of a hiking outfit.

I claim:

1. A conveniently transportable emergency kit for use in adverse environmental conditions, comprising:
   a pouch dimensioned to receive the head of a user and composed of a synthetic resin foil having a gold metallic outer surface and a silver metallic inner surface;
   folded rectangular sheet of synthetic resin foil received in said pouch and dimensioned to wrap around the body of a user, said foil being composed of synthetic resin and having a silver metallized surface adapted to reflect body heat back to the user and a gold metallized surface adapted to be readily detected by the rescuer; and
   a supply of vitamins capable of sustaining life in the absence of other sustenance for an extended period received in said pouch.

2. The kit defined in claim 1 wherein said sheet has a central hole adapted to pass over the head of the user and enables said sheet to be wrapped as a poncho around the body of the user.

* * * * *